(12) United States Patent
Yukimoto

(10) Patent No.: US 9,415,128 B2
(45) Date of Patent: Aug. 16, 2016

(54) MOVING HANDRAIL DISINFECTING DEVICE FOR PASSENGER CONVEYOR

(71) Applicant: Toshihiro Yukimoto, Osaka (JP)

(72) Inventor: Toshihiro Yukimoto, Osaka (JP)

( * ) Notice: Subject to any disclaimer, the term of this patent is extended or adjusted under 35 U.S.C. 154(b) by 471 days.

(21) Appl. No.: 14/138,995

(22) Filed: Dec. 23, 2013

(65) Prior Publication Data

US 2014/0186221 A1 Jul. 3, 2014

(30) Foreign Application Priority Data

Dec. 28, 2012 (JP) ................. 2012-288872

(51) Int. Cl.
*A61L 2/24* (2006.01)
*A61L 2/18* (2006.01)
*B66B 31/02* (2006.01)

(52) U.S. Cl.
CPC ... *A61L 2/24* (2013.01); *A61L 2/18* (2013.01); *B66B 31/02* (2013.01)

(58) Field of Classification Search
CPC ...................................... B66B 31/02
USPC ........................................ 198/495
See application file for complete search history.

(56) References Cited

FOREIGN PATENT DOCUMENTS

| JP | 5-51194 | 3/1993 |
|---|---|---|
| JP | 5-338984 | 12/1993 |
| JP | 8-119569 | 5/1996 |
| JP | 2004-113729 | 4/2004 |
| JP | 2004-277462 | 10/2004 |
| JP | 2005-132532 | 5/2005 |
| JP | 2007-314298 | 12/2007 |
| JP | 2008-63103 | 3/2008 |
| JP | 2008-280141 | 11/2008 |
| JP | 2011-121664 | 6/2011 |
| JP | 2012-197154 | 10/2012 |

OTHER PUBLICATIONS

English-language machine translation of JP 05-051194.*

* cited by examiner

*Primary Examiner* — Timothy Cleveland
(74) *Attorney, Agent, or Firm* — Wenderoth, Lind & Ponack, L.L.P.

(57) ABSTRACT

A moving handrail disinfecting device for passenger conveyor which enables a reduction in burden of maintenance, leading to improved maintenance performance of the device, wherein information concerning the device is centrally managed in a management center so as to enhance shareability of information, leading to improved maintenance performance of the whole system, is a moving handrail disinfecting device 10 for disinfecting a moving handrail 5 of an escalator 1, having a disinfecting unit comprising a plurality of applying members 11 for disinfecting the surface of the moving handrail 5, being installed outside an inlet part 6A of the moving handrail 5, an applying member replacing mechanism, a disinfection solution supplier 24 and associated parts, a control unit 60 operable to control disinfection operations by the disinfecting unit based on a dirt detection state by a dirt detecting unit 40, and a communications unit 50 operable to send information concerning said disinfecting device 10 to an outside management center 100.

12 Claims, 11 Drawing Sheets

MOVING HANDRAIL DISINFECTING DEVICE FOR PASSENGER CONVEYOR

BACKGROUND OF THE INVENTION

1. Field of the Invention

The present invention relates to a moving handrail disinfecting device for passenger conveyor, and more particularly, to a moving handrail disinfecting device for passenger conveyor which can disinfect moving handrails of passenger conveyors such as escalators and moving pavements.

2. Description of the Relevant Art

In the public facilities and commercial facilities such as the stations and department stores, escalators are placed. An escalator has endless moving handrails which circuit in synchronism with steps (treadboards) on which users stand on both sides thereof. In order to use the escalator safely, the users preferably get on the steps with holding onto the moving handrail and keep on holding onto the moving handrail until they get off.

However, since the moving handrails of the escalators are held by large numbers of the general public, some of the users do not like to touch the moving handrails. Especially in the season of the spread of influenza or the like, there are a lot of users who get on the escalators with trying not to touch the moving handrails thereof in fear of a virus infection through the medium of the moving handrails.

Therefore, disinfecting devices for moving handrails of passenger conveyors have been proposed. For example, in the below-mentioned Patent Document 1, a device has been disclosed, having a roller which disinfects the surface of a moving handrail in the vicinity of an inlet of the moving handrail within a truss. Using this disinfecting device, when a user who came to a landing of an escalator is detected by a sensor, the moving handrail is disinfected by allowing the roller to make contact with the moving handrail only during the interval that the moving handrail makes a circuit.

However, using the disinfecting device described in the Patent Document 1, every time a user of the escalator is detected, the disinfection by the roller is conducted. As a result, in places where there are a lot of passengers, the disinfection by the roller is likely to be continuously conducted. Therefore, there is a problem that the roller and associated parts which make contact with the moving handrail are quickly deteriorated. Moreover, since the roller is arranged within the truss, there is another problem that maintenance work such as replacement of those parts is not easy to perform.

Using the disinfecting device described in the Patent Document 1, since the disinfection is conducted without regard to a sticking state of dirt (tiny dirt such as dust, oil element, etc.), viruses and the like to the moving handrail, the frequency of refilling of a disinfection solution and that of replacement of the roller tend to be high, leading to a problem of a high maintenance cost.

In the case of a large facility, a dozen or more escalators are placed in the whole facility. Supposing that the disinfecting devices described in the Patent Document 1 are installed on every escalator in such facility, since the number of users of each escalator varies depending on its arranged place, the disinfecting devices installed on each escalator vary in degree of deterioration of the roller and that of dirt, and in decrease of the disinfection solution and the like. However, since these situations of each disinfecting device cannot be seen from the outside of the disinfecting device, it is necessary to uniformly perform maintenance work on every disinfecting device. Therefore, since the burden of such maintenance work is heavy and it is impossible to appropriately manage every disinfecting device, it is difficult to actually install such disinfecting devices.

Patent Document 1: Japanese Patent Application Laid-Open Publication No. 2011-121664

SUMMARY OF THE INVENTION

The present invention was developed in order to solve the above problems, and it is an object of the present invention to provide a moving handrail disinfecting device for passenger conveyor, which enables a reduction in burden of maintenance work, leading to improved maintenance performance of the device, wherein information concerning the device is centrally managed in a management center so as to enhance shareability of information, leading to improved maintenance performance of the whole system.

In order to achieve the above object, a moving handrail disinfecting device for passenger conveyor according to a first aspect of the present invention is characterized by being a moving handrail disinfecting device for disinfecting a moving handrail circuiting in synchronism with steps of a passenger conveyor, comprising a disinfecting unit operable to disinfect the surface of the moving handrail, being installed outside at least one of handrail inlets on each side of drawing and delivery of the moving handrail, a control unit operable to control disinfection operations by the disinfecting unit based on prescribed operating conditions, and a communications unit operable to send information obtained by said disinfecting device to an outside management center, the disinfecting unit comprising a storage section which can separately store a plurality of applying members, a disinfection solution supply section operable to hold an applying member taken from said storage section, as well as supply a disinfection solution to said held applying member, and an applying member replacing section having a function of allowing the disinfection solution supply section to hold the applying member stored in the storage section, as well as a function of putting the applying member held by the disinfection solution supply section into the storage section, wherein the applying member held by the disinfection solution supply section is allowed to make contact with the surface of the moving handrail to apply the disinfection solution.

By the moving handrail disinfecting device for passenger conveyor according to the first aspect of the present invention, since the disinfecting unit is installed outside the handrail inlet, maintenance work of said disinfecting device can be easily performed. Owing to the control unit, based on the prescribed operating conditions, it becomes possible to appropriately conduct the disinfection operations by the disinfecting unit. By the applying member replacing section constituting the disinfecting unit, an applying member stored in the storage section (i.e. an applying member for replacement) can be held by (mounted on) the disinfection solution supply section and the (used) applying member held by (mounted on) the disinfection solution supply section can be put into the storage section. That is, since the replacement of the plurality of applying members can be automatically conducted without manual operation, the burden of maintenance can be reduced, leading to improved maintenance performance.

Since various kinds of information obtained by said disinfecting device is sent to the outside management center by the communications unit, for example, the management center can centrally manage information concerning a plurality of disinfecting devices installed on each passenger conveyor in a facility. Based on these items of information, it becomes possible to perform appropriate maintenance on every disinfecting device, leading to improved shareability of information and maintenance performance of the whole system.

The moving handrail disinfecting device for passenger conveyor according to a second aspect of the present invention is characterized by the disinfection solution supply section constituting the disinfecting unit, having a first reservoir which can reserve a first disinfection solution and a second reservoir which can reserve a second disinfection solution, and the control unit, separately controlling the timing of supplying the first disinfection solution to the first reservoir and the timing of supplying the second disinfection solution to the second reservoir in the moving handrail disinfecting device for passenger conveyor according to the first aspect of the present invention.

By the moving handrail disinfecting device for passenger conveyor according to the second aspect of the present invention, since the disinfection solution supply section has the first reservoir and the second reservoir, two sorts of disinfection solutions can be supplied to the applying member. Since the timing of supplying the first disinfection solution to the first reservoir and the timing of supplying the second disinfection solution to the second reservoir are separately controlled, it is possible to suitably use the first disinfection solution and the second disinfection solution depending on the situations of said disinfecting device and conduct appropriate disinfection treatment with little waste.

The moving handrail disinfecting device for passenger conveyor according to a third aspect of the present invention is characterized by further comprising a dirt detecting unit operable to detect dirt on the surface of the moving handrail, wherein the control unit controls the timing and time of a disinfection operation by the disinfecting unit based on the state of dirt detected by the dirt detecting unit, as well as controls the communications unit to send information about the state of dirt detected by the dirt detecting unit to the management center in the moving handrail disinfecting device for passenger conveyor according to the first or second aspect of the present invention.

By the moving handrail disinfecting device for passenger conveyor according to the third aspect of the present invention, since the timing and time of a disinfection operation by the disinfecting unit is controlled based on the state of dirt detected by the dirt detecting unit, it is possible to conduct disinfection of the moving handrail at an appropriate frequency based on the state of dirt. As a result, it is possible to prevent disinfection treatment from being conducted more than necessary, leading to a reduction in maintenance cost such as disinfection solution cost. In the management center, information about the state of dirt detected by the dirt detecting unit of each disinfecting device can be managed, and therefore, it becomes possible to perform required maintenance work with proper timing on every disinfecting device.

The moving handrail disinfecting device for passenger conveyor according to a fourth aspect of the present invention is characterized by further comprising a passenger number detecting unit operable to detect the number of persons boarding the passenger conveyor, wherein the control unit controls the timing and time of a disinfection operation by the disinfecting unit based on the accumulated number of passengers detected by the passenger number detecting unit, as well as controls the communications unit to send information about the accumulated number of passengers detected by the passenger number detecting unit to the management center in the moving handrail disinfecting device for passenger conveyor according to the first or second aspect of the present invention.

By the moving handrail disinfecting device for passenger conveyor according to the fourth aspect of the present invention, since the timing and time of a disinfection operation by the disinfecting unit is controlled based on the accumulated number of passengers detected by the passenger number detecting unit, it is possible to conduct disinfection of the moving handrail at an appropriate frequency based on the accumulated number of passengers. As a result, it is possible to prevent disinfection treatment from being conducted more than necessary, leading to a reduction in maintenance cost such as disinfection solution cost. In the management center, the accumulated number of passengers detected by the passenger number detecting unit of each disinfecting device can be managed, and therefore, it becomes possible to perform required maintenance work with proper timing on every disinfecting device.

The moving handrail disinfecting device for passenger conveyor according to a fifth aspect of the present invention is characterized by further comprising a handrail contact detecting unit operable to detect a contact of a part of a body with the moving handrail, wherein the control unit controls the timing and time of a disinfection operation by the disinfecting unit based on the detection state of handrail contact detected by the handrail contact detecting unit, as well as controls the communications unit to send information about the detection state of handrail contact detected by the handrail contact detecting unit to the management center in the moving handrail disinfecting device for passenger conveyor according to the first or second aspect of the present invention.

By the moving handrail disinfecting device for passenger conveyor according to the fifth aspect of the present invention, since the timing and time of a disinfection operation by the disinfecting unit is controlled based on the detection state of handrail contact detected by the handrail contact detecting unit, it is possible to separately conduct disinfection of each moving handrail arranged on the right and left sides at an appropriate frequency based on the detection state of handrail contact, such as the accumulated number of persons who made contact with the moving handrail. As a result, it is possible to prevent disinfection treatment from being conducted more than necessary, leading to a reduction in maintenance cost such as disinfection solution cost. In the management center, the detection state of handrail contact detected by the handrail contact detecting unit of each disinfecting device can be managed, and therefore, it becomes possible to perform required maintenance work with proper timing on every disinfecting device.

The moving handrail disinfecting device for passenger conveyor according to a sixth aspect of the present invention is characterized by further comprising a virus detecting unit operable to detect a prescribed virus sticking to the surface of the moving handrail, wherein the control unit controls the timing and time of a disinfection operation by the disinfecting unit based on the detection state of the virus detected by the virus detecting unit, as well as controls the communications unit to send information about the detection state of the prescribed virus detected by the virus detecting unit to the management center in the moving handrail disinfecting device for passenger conveyor according to the first or second aspect of the present invention.

Using the moving handrail disinfecting device for passenger conveyor according to the sixth aspect of the present invention, since the timing and time of a disinfection operation by the disinfecting unit is controlled based on the detection state of the virus detected by the virus detecting unit, it is possible to conduct sufficient disinfection with good timing in the case of high necessity of disinfection on public health, according to the detection state of the virus, for example, in a case where the influenza virus, the noro-virus or the like was detected, leading to an improvement in public health. In the management center, the detection state of the virus detected by the virus detecting unit of each disinfecting device can be managed, and therefore, it becomes possible to know which passenger conveyor highly needs to be disinfected and to perform required maintenance work such as replacement with a suitable disinfection solution with proper timing on every disinfecting device.

A moving handrail disinfecting device for passenger conveyor according to a seventh aspect of the present invention is characterized by being a moving handrail disinfecting device for disinfecting a moving handrail circuiting in synchronism with steps of a passenger conveyor, comprising a disinfecting unit operable to disinfect the surface of the moving handrail, being installed outside at least one of handrail inlets on each side of drawing and delivery of the moving handrail, and a control unit operable to control disinfection operations by the disinfecting unit based on prescribed operating conditions, the disinfecting unit comprising a storage section which can separately store a plurality of applying members, a disinfection solution supply section operable to hold an applying member taken from said storage section, as well as supply a disinfection solution to said held applying member, and an applying member replacing section having a function of allowing the disinfection solution supply section to hold the applying member stored in the storage section, as well as a function of putting the applying member held by the disinfection solution supply section into the storage section, wherein the applying member held by the disinfection solution supply section is allowed to make contact with the surface of the moving handrail to apply the disinfection solution.

When the moving handrail disinfecting device for passenger conveyor according to the seventh aspect of the present invention is used, by the applying member replacing section constituting the disinfecting unit, an applying member stored in the storage section (i.e. an applying member for replacement) can be held by (mounted on) the disinfection solution supply section and the (used) applying member held by the disinfection solution supply section can be put into the storage section. That is, since the replacement of the applying members can be automatically conducted without manual operation, the burden of maintenance can be reduced, leading to improved maintenance performance.

The moving handrail disinfecting device for passenger conveyor according to an eighth aspect of the present invention is characterized by the disinfection solution supply section constituting the disinfecting unit, having a first reservoir which can reserve a first disinfection solution and a second reservoir which can reserve a second disinfection solution, and the control unit, separately controlling the timing of supplying the first disinfection solution to the first reservoir and the timing of supplying the second disinfection solution to the second reservoir in the moving handrail disinfecting device for passenger conveyor according to the seventh aspect of the present invention.

By the moving handrail disinfecting device for passenger conveyor according to the eighth aspect of the present invention, since the disinfection solution supply section has the first reservoir and the second reservoir, two sorts of disinfection solutions can be supplied to the applying member. Since the timing of supplying the first disinfection solution to the first reservoir and the timing of supplying the second disinfection solution to the second reservoir are separately controlled, it is possible to suitably use the first disinfection solution and the second disinfection solution depending on the situations of said disinfecting device and conduct appropriate disinfection treatment with little waste.

DESCRIPTION OF THE PREFERRED EMBODIMENTS

Figure 1:
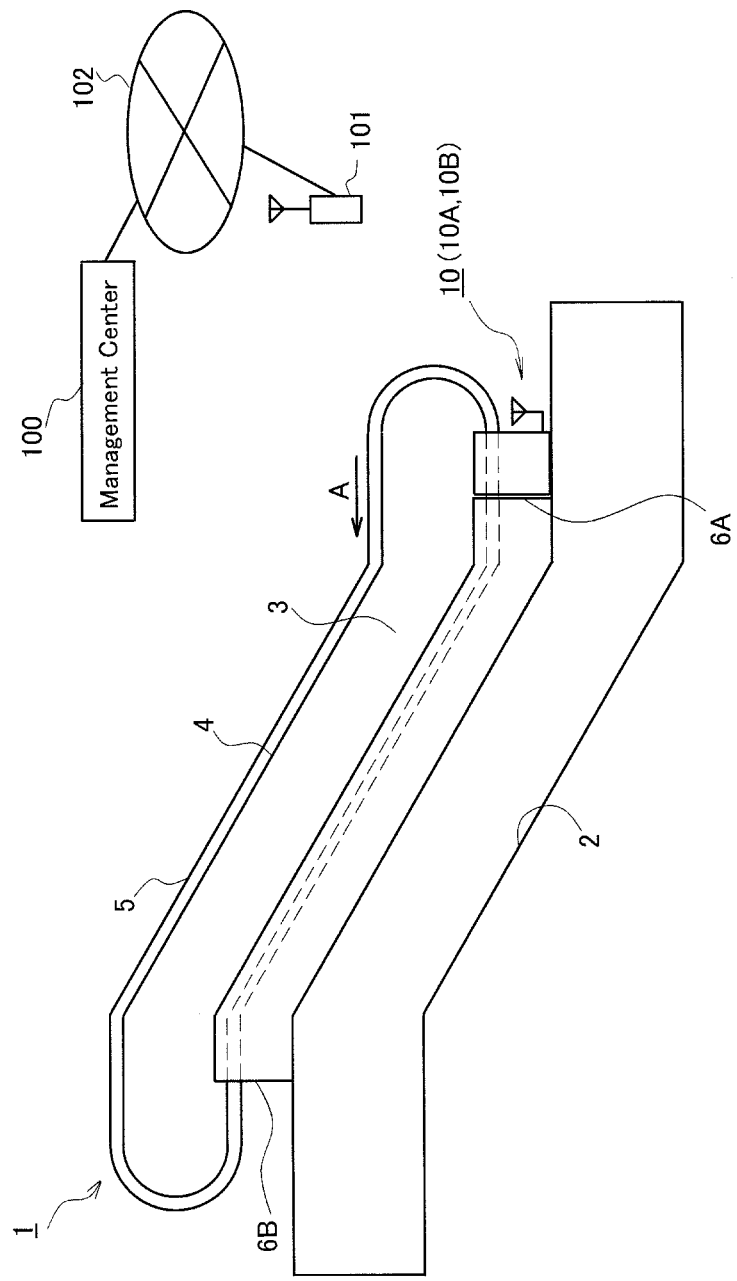
FIG. 1 is a side view schematically showing the main part of a passenger conveyor equipped with a moving handrail disinfecting device for passenger conveyor according to a first embodiment of the present invention.

The preferred embodiments of the moving handrail disinfecting device for passenger conveyor according to the present invention are described below by reference to the Figures noted above. FIG. 1 is a side view schematically showing the main part of an escalator equipped with a moving handrail disinfecting device for passenger conveyor (hereinafter, referred to as a moving handrail disinfecting device) according to a first embodiment.

An escalator 1 comprises a foundation (hereinafter, referred to as a truss) 2 built with a steel frame which supports the whole escalator from the bottom, wherein a lot of steps (not shown) moving in a line between the upper floor and the lower floor are arranged. These not shown steps are members having treadboard surfaces which users get on. Within the truss 2, a driving unit (not shown) including a motor, a speed reducer and associated parts, and an escalator control unit (not shown) which controls the whole escalator including said driving unit are also arranged.

On both sides of the not shown steps arranged in the truss 2, balustrades 3 made of a metal plate or a resin plate each stand. On the outer peripheral portion of the balustrade 3, a guide rail 4 is arranged, and an endless moving handrail 5 is caused to circuit in synchronism with the not shown steps along this guide rail 4. Users can get on the escalator 1 by standing on the not shown steps with holding onto the moving handrail 5.

Here, a case wherein the escalator 1 is going up, that is, a case wherein the moving handrail 5 is moving in the direction of an arrow A is described.

The moving handrail 5 goes through an inlet part (delivery inlet) 6A on the lower floor side (handrail delivery side) of the truss 2 to the outside of the truss 2, turns up in a landing of the lower floor, moves along the guide rail 4 on the upper peripheral portion of the balustrade 3 in the direction of the arrow A, turns down again in a landing of the upper floor, enters the truss 2 through an inlet part (drawing inlet) 6B formed on the upper floor side (handrail drawing side) of the truss 2, and circuits through the truss 2 to the inlet part 6A in the lower floor landing.

Outside both of the inlet parts 6A on the lower floor side, moving handrail disinfecting devices 10 each are installed. Here, the moving handrail disinfecting devices 10 are preferably installed outside the inlet parts 6A on the lower floor side in the case of an up-escalator, while outside the inlet parts 6B on the upper floor side in the case of a down-escalator, but the form of installation thereof is not limited to this. The moving handrail disinfecting devices 10 may be installed outside the inlet parts 6A and 6B on both of the upper and lower floor sides.

How to set the moving handrail disinfecting device 10 is not particularly limited. Attachment to the floor, attachment to the side surface of the inlet part 6A, or making a clip such as a heavy-duty clip on the top of the device by which one-touch attachment to the balustrade 3 is made possible, may be adopted.

The moving handrail disinfecting device 10 can exchange data with a management center 100 through a base station 101 and a communication network 102 such as the Internet communication network and a telephone network. The outside management center 100, corresponding to an information management center inside the facility wherein the escalator 1 is placed, or an information management center managing the escalator 1 outside the facility, comprises a computer system including a server and the like.

Figure 2:
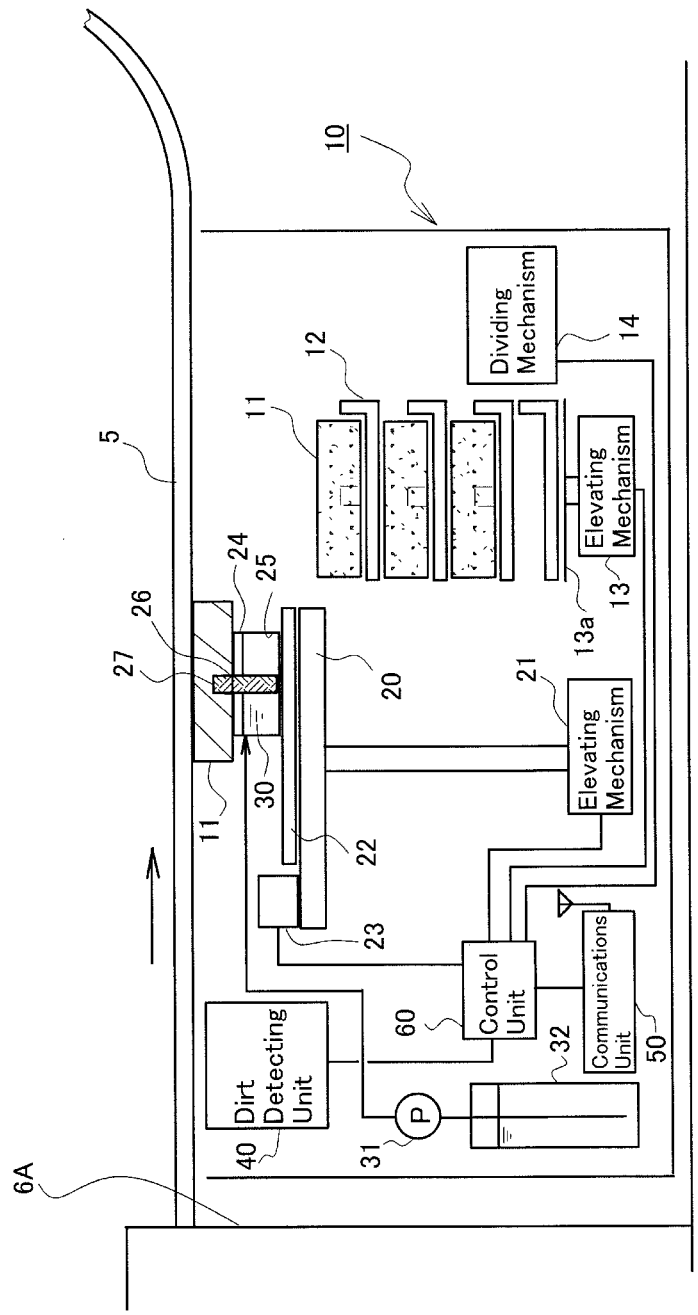
FIG. 2 is a side view schematically showing the main part of the moving handrail disinfecting device for passenger conveyor according to the first embodiment.

FIG. 2 is a side view schematically showing the main part of the moving handrail disinfecting device according the first embodiment. The moving handrail disinfecting device 10 comprises a plurality of holding frames 12 as a storage wherein applying members 11 for replacement are held (stored), an elevating mechanism 13 to raise and lower the layered holding frames 12, and a dividing mechanism 14 to divide these holding frames 12 at a prescribed point.

The moving handrail disinfecting device 10 comprises a stand 20, an elevating mechanism 21 to raise and lower the stand 20, a slide plate 22 arranged on the stand 20, a sliding mechanism 23 to horizontally move the slide plate 22 toward the holding frames 12, and a disinfection solution supplier 24 (a disinfection solution supply section) located on the slide plate 22, wherein the applying member 11 is mounted on the disinfection solution supplier 24.

An applying member replacing unit comprises the elevating mechanism 13, dividing mechanism 14, elevating mechanism 21 and sliding mechanism 23, and as these mechanisms, an electromagnetic actuator having a stretching mechanism, a motor-driven cam mechanism, or various kinds of driving mechanisms made by combining a gear mechanism such as a worm gear or a rack and pinion with a motor may be adopted. A disinfecting unit comprises the above applying members 11, plural holding frames 12, elevating mechanism 13, dividing mechanism 14, elevating mechanism 21, sliding mechanism 23 and disinfection solution supplier 24.

The disinfection solution supplier 24 comprises a reservoir 25 wherein a disinfection solution 30 is reserved, to which a disinfection solution tank 32 is connected through a pump 31. The disinfection solution 30 is supplied to the reservoir 25 with prescribed timing (e.g. the timing when it is detected that the liquid surface came to a predetermined level or lower by a not shown level sensor which detects the liquid surface level arranged in the reservoir 25).

On the top of the disinfection solution supplier 24, a projecting opening 26 is formed, wherein a bar-shaped liquid absorbing member 27 made of a felt, a sponge, a fiber with a high liquid absorptivity or the like is fit. Through the liquid absorbing member 27, the disinfection solution 30 in the reservoir 25 is supplied to (absorbed by) the applying member 11. Here, the opening 26 and liquid absorbing member 27 may be arranged in two or more places, and by such construction, the mounting stability of the applying member 11 can be improved, and it becomes possible to more easily regulate the quantity of liquid absorption.

As the disinfection solution 30, various kinds of disinfection/sterilization solutions such as an alcohol formulation having a disinfecting/sterilizing property such as ethanol, a solution containing iodine of a prescribed concentration (e.g. about 1% of iodine) and a benzalkonium chloride solution of a prescribed concentration (e.g. about 0.05%-0.1%) are applied.

The moving handrail disinfecting device 10 further comprises a dirt detecting unit 40 which detects the state of dirt sticking to the surface of the moving handrail 5. The dirt detecting unit 40 comprises an image sensor for visual inspections, an image processor and associated parts, having a function of continuously or periodically monitoring the state of foreign materials such as small dirt (dust) or oil element sticking to the surface and the degree (sticking range, sticking number, etc.) thereof, whereby detection signals of dirt and the like are output to a control unit 60.

The moving handrail disinfecting device 10 further comprises a communications unit 50 for communications with the outside management center 100. The communications unit 50 has a function of wireless communications which makes it possible to exchange data with the management center 100 through the base station 101 and the communication network 102 such as the Internet communication network and the telephone network shown in FIG. 1. Here, the communications unit 50 may also have a function of cable communications.

The moving handrail disinfecting device 10 comprises the control unit 60 which conducts control such as operation control and data sending/receiving control on the above elevating mechanism 13, dividing mechanism 14, elevating mechanism 21, sliding mechanism 23, pump 31, dirt detecting unit 40 and communications unit 50. The control unit 60 comprises a not shown microcomputer, an input/output interface, a memory, a timer circuit, a power circuit and associated parts.

An operation of replacement of the applying members 11 conducted by the moving handrail disinfecting device 10 according to the first embodiment is described below. The moving handrail disinfecting device 10 shown in FIG. 2 has four holding frames 12, and the applying member 11 which had been held in the lowest holding frame 12 has been mounted on the disinfection solution supplier 24.

Figure 3:
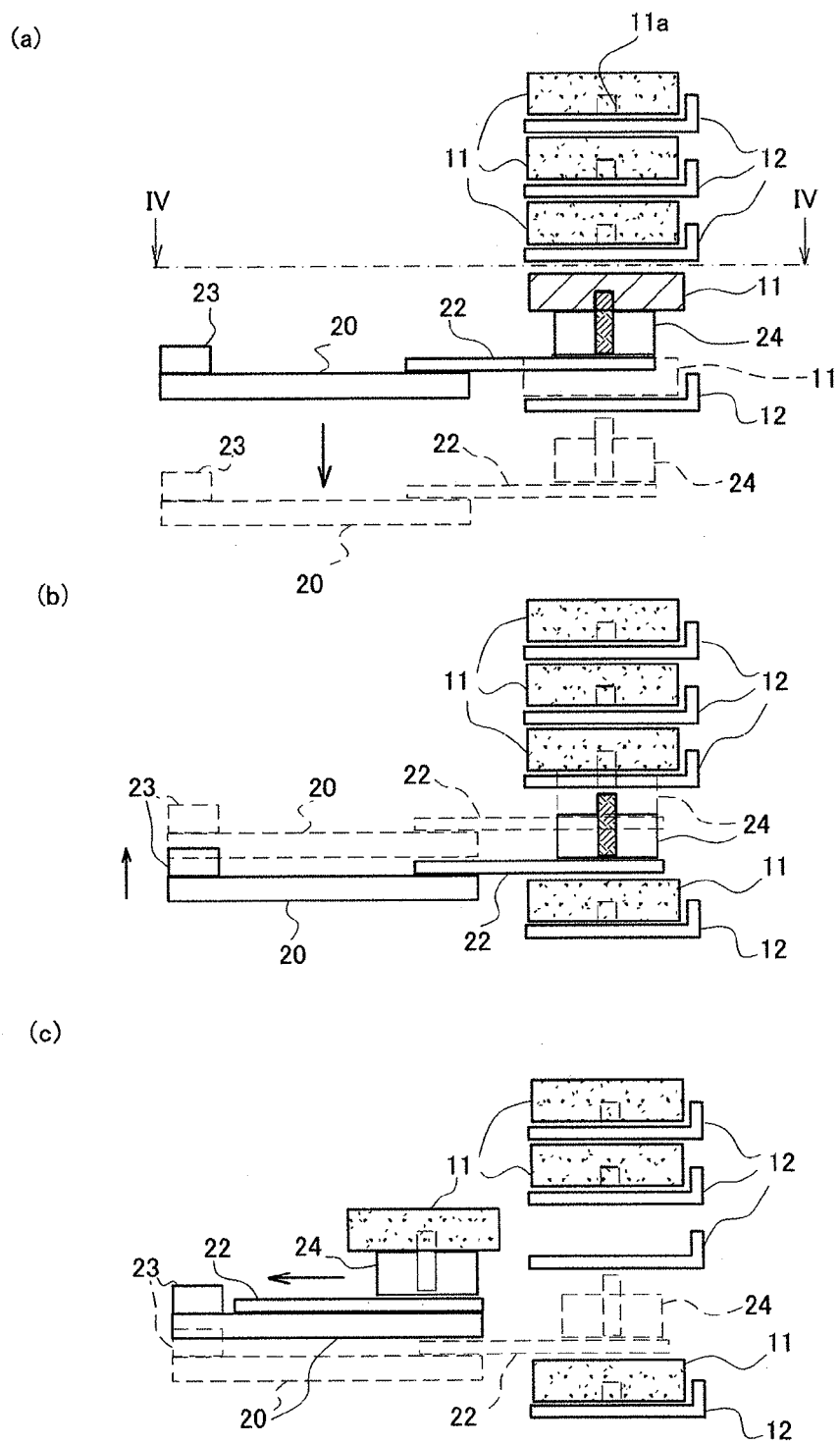
FIG. 3(a) is a side view of the main part to illustrate an operation of putting a used applying member into the lowest holding frame, and FIGS. 3(b) and 3(c) each are side views of the main part to illustrate an operation of mounting an applying member in the second lowest holding frame on a disinfection solution supplier.

FIG. 3(a) is a side view of the main part to illustrate an operation of putting the used applying member 11 into the lowest holding frame 12, and FIGS. 3(b) and 3(c) each are side views of the main part to illustrate an operation of mounting the applying member 11 in the second lowest holding frame 12 on the disinfection solution supplier 24.

Figure 4:
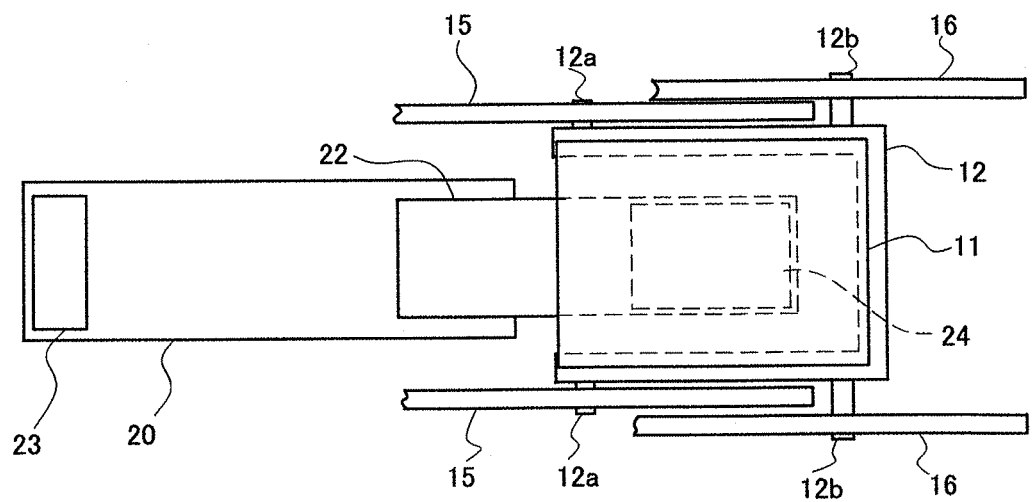
FIG. 4 is a plan view of the main part seen along a IV-IV line of FIG. 3(a)
Figure 5:
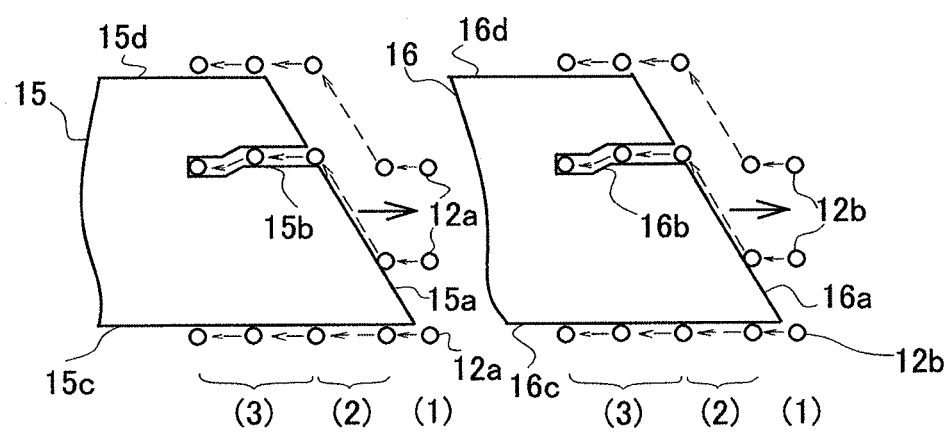
FIG. 5 is a side view of the main part to illustrate a dividing mechanism of holding frames.

FIG. 4 is a plan view of the main part seen along a IV-IV line of FIG. 3(a). FIG. 5 is a side view of the main part to illustrate the dividing mechanism 14 of the holding frames 12.

As shown in FIG. 4, the holding frame 12 is formed almost in a square-cornered U-shape seen in a plane, being a shape (having an L-shaped section) which makes it possible to support the applying member 11 in an almost rectangular parallelepiped shape in a manner that encloses the peripheral portions of three sides of the bottom thereof. On both sides of the holding frame 12, dividing projections 12a and 12b for raising/lowering and dividing the holding frames 12 in engagement with dividing slide plates 15 and 16 are formed. Here, the applying member 11 may be formed with the top almost in a U-shape, which makes it possible to make contact with the side of the moving handrail 5 having an almost C-shaped section.

The elevating mechanism 13 has a function of raising/lowering a bottom plate 13a arranged underneath the lowest holding frame 12, which makes it possible to raise or lower all the plurality of holding frames 12 to a prescribed position.

The dividing slide plates 15 and 16 constituting the dividing mechanism 14 are slidably attached to the side walls or the like of a case of the device, which slide by use of a driving force such as a motor.

As shown in FIG. 5, the dividing slide plates 15 and 16 comprise incline portions 15a and 16a with which the dividing projections 12a and 12b are engaged, and guide grooves 15b and 16b which guide the dividing projections 12a and 12b. The guide grooves 15b and 16b are formed for keeping the division space of the holding frames 12 uniform, in the position of a fixed height which makes it possible to form a space into which the slide plate 22 and the disinfection solution supplier 24 can advance.

In the case of storing the applying member 11 mounted on the disinfection solution supplier 24 in the lowest holding frame 12, the elevating mechanism 13 and the dividing mechanism 14 are actuated to divide the holding frames 12 in such a manner that a prescribed space is formed between the lowest holding frame 12 and the second lowest holding frame 12.

That is, by actuating the elevating mechanism 13, the whole holding frames 12 are raised in such a manner that the lower ends of the incline portions 15a and 16a of the dividing slide plates 15 and 16 are located between the lowest holding frame 12 and the second lowest holding frame 12 (the situation of FIG. 5(1)).

Then, under the situation where the lower ends of the incline portions 15a and 16a of the dividing slide plates 15 and 16 are located between the lowest holding frame 12 and the second lowest holding frame 12, the dividing slide plates 15 and 16 are caused to slide.

As shown in FIG. 5, the dividing projections 12a and 12b of the lowest holding frame 12 move along the bottom sides 15c and 16c of the dividing slide plates 15 and 16, while the dividing projections 12a and 12b of the second lowest holding frame 12 elevate along the incline portions 15a and 16a of the dividing slide plates 15 and 16 (the situation of FIG. 5(2)). Thereafter, by being guided by the guiding grooves 15b and 16b, the lowest holding frame 12 and the second lowest holding frame 12 are divided with a prescribed space (the situation of FIG. 5(3)).

The dividing projections 12a and 12b of the third holding frame 12 from the bottom move along the top sides 15d and 16d of the dividing slide plates 15 and 16. Here, by the step portions in the middle of the guide grooves 15b and 16b, the third holding frame 12 from the bottom does not directly mount on the applying member 11 stored in the second lowest holding frame 12.

After completing the division of the holding frames 12, as shown in FIG. 3(a), the elevating mechanism 21 is actuated to lower the stand 20 in such a manner that the applying member 11 is located between the lowest holding frame 12 and the second lowest holding frame 12 which were divided. Thereafter, the sliding mechanism 23 is actuated to slide the slide plate 22 to a prescribed position within the divided space (a position where the applying member 11 can be mounted on the lowest holding frame 12).

Then, the elevating mechanism 21 is actuated to allow the applying member 11 to be held on the lowest holding frame 12 and lower the stand 20 to a position where the applying member 11 gets out of the disinfection solution supplier 24. This is the completion of the operation of storing the used applying member 11 in the lowest holding frame 12.

Thereafter, the sliding mechanism 23 is actuated to slide the slide plate 22 to its original position, and the elevating mechanism 21 is actuated again, as shown in FIG. 3(b), to raise the stand 20 to a position where the slide plate 22 and the disinfection solution supplier 24 can be allowed to enter between the lowest holding frame 12 and the second lowest holding frame 12 which were divided.

Then, the sliding mechanism 23 is actuated to slide the slide plate 22 to a prescribed position within the divided space (where the liquid absorbing member 27 of the disinfection solution supplier 24 can be put into a hole 11a on the bottom of the applying member 11).

Thereafter, the elevating mechanism 21 is actuated to raise the stand 20 to a position where the liquid absorbing member 27 of the disinfection solution supplier 24 is put into the hole 11a on the bottom of the applying member 11 and mount a new applying member 11 on the disinfection solution supplier 24.

After mounting thereof, the sliding mechanism 23 is actuated to slide the slide plate 22 to its original position (FIG. 3(c)), and thereafter, the elevating mechanism 21 is actuated to raise the stand 20 to a fixed position of the disinfection operation. This is the completion of the replacement operation of the applying members 11.

Figure 6:
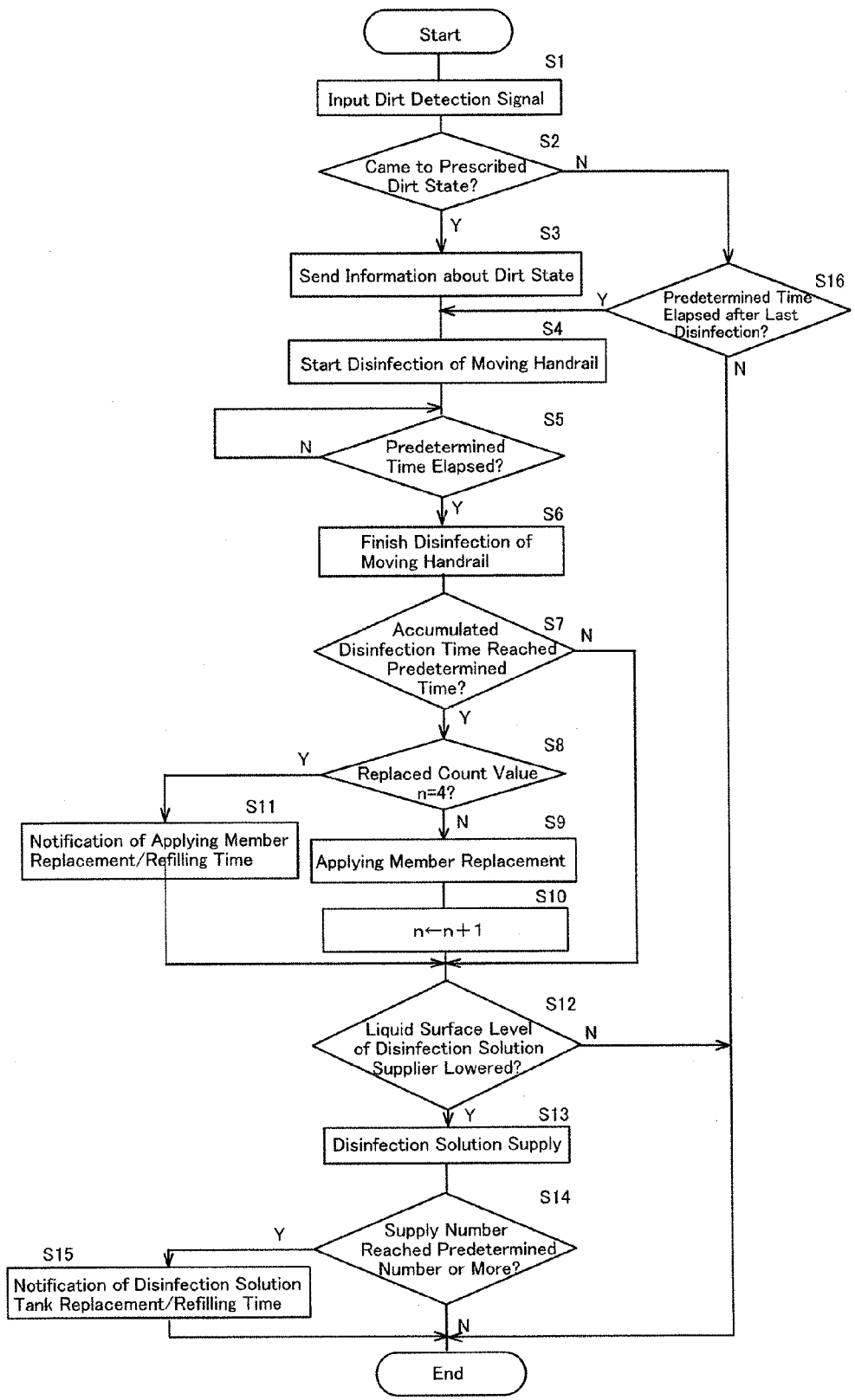
FIG. 6 is a flowchart showing a treatment operation conducted by a control unit in the moving handrail disinfecting device for passenger conveyor according to the first embodiment.

FIG. 6 is a flowchart showing a treatment operation conducted by the control unit 60 in the moving handrail disinfecting device 10 according to the first embodiment.

In Step S1, a dirt detection signal is input from the dirt detecting unit 40, and in Step S2, whether the surface of the moving handrail 5 came to a prescribed dirt state or not (e.g. whether the detected number of sticking foreign materials such as dirt reached a predetermined number after the last disinfection operation or not) is judged. When it is judged that it came to the prescribed dirt state (e.g. the detected number of sticking foreign materials reached the predetermined number), the operation goes to Step S3.

In Step S3, the communications unit 50 is controlled to send information concerning the dirt state (e.g. identification information about the device itself, elapsed time information after the last disinfection operation, and information including the detected number of sticking foreign materials) to the outside management center 100, and the operation goes to Step S4.

In Step S4, disinfection treatment on the moving handrail 5 using the applying member 11 moistened with the disinfection solution 30 is started. That is, the elevating mechanism 21 is actuated to conduct control to raise the stand 20 to a situation where the applying member 11 is in contact with (is pressed against) the moving handrail 5. In Step S5, whether a predetermined time elapsed or not is judged, and when it is judged that the predetermined time elapsed, the operation goes to Step S6.

In Step S6, the elevating mechanism 21 is actuated to lower the stand 20 to a prescribed position where the applying member 11 which has been in contact with the moving handrail 5 comes off (is brought out of contact with) the moving handrail 5. This is the completion of the disinfection treatment on the moving handrail 5 using the applying member 11. Here, the above-mentioned predetermined time is set to a previously decided uniform time, a time required for the moving handrail 5 to circuit a fixed number of times, a time decided depending on the state of dirt or the like.

The operation goes to Step S7, wherein whether an accumulated time of the disinfection operation using the presently using applying member 11 reached a predetermined time (e.g. a given time from several hours to several ten hours or so) or not is judged. When it is judged that it has not reached the predetermined time, the operation goes to Step S12, while when it is judged that it reached the predetermined time, the operation goes to Step S8.

In Step S8, whether a count value n of replaced applying members 11 equals four (4) or not is judged, and when it is judged that n does not equal four (4), that is, there is an (are) unused applying member(s) 11, the operation goes to Step S9. In Step S9, by controlling the elevating mechanism 13, dividing mechanism 14, elevating mechanism 21 and sliding mechanism 23, an automatic replacement operation of the applying members 11 is conducted. In Step S10, one (1) is added to the count value n of replaced applying members 11, and the operation goes to Step S12.

On the other hand, in Step S8, when it is judged that the count value n of replaced applying members 11 equals four (4), that is, there is no unused applying member 11, the operation goes to Step S11. In Step S11, the communications unit 50 is controlled to send a signal notifying that the replacement/refilling time of the applying members 11 has come, identification information about the device itself and the like to the outside management center 100, and thereafter, the operation goes to Step S12. Here, when the replacement/refilling of the applying members 11 was conducted, the count value n of replaced applying members 11 is initialized. Since these holding frames 12 and applying members 11 are kept in one cartridge (frame), the whole cartridge can be easily replaced with another one.

In Step S12, whether a detection signal of lowered liquid surface level of the disinfection solution supplier 24 was detected or not is judged. When it is judged that the detection signal of lowered liquid surface level was detected, the operation goes to Step S13, wherein the pump 31 is actuated for a predetermined time to supply a prescribed amount of the disinfection solution 30 from the disinfection solution tank 32.

In Step S14, whether the number of supplies of the disinfection solution 30 after replacement of the disinfection solution tank 32 reached a predetermined number thereof or not is judged. When it is judged that it has not reached the predetermined number thereof, the treatment is finished, while when it is judged that it reached the predetermined number thereof (i.e. the time of replacement/refilling of the disinfection solution tank 32 has come), the operation goes to Step S15. In Step S15, the communications unit 50 is controlled to send information notifying that the time of replacement/refilling of the disinfection solution tank 32 has come, identification information about the device itself and the like to the outside management center 100. Here, when the replacement/refilling of the disinfection solution tank 32 was conducted, the count value of the number of supplies is initialized.

On the other hand, in Step S2, when it is judged that the surface of the moving handrail 5 has not come to the prescribed dirt state, the operation goes to Step S16, wherein whether a predetermined time elapsed after the last disinfection operation or not is judged. When it is judged that the predetermined time has not elapsed, the treatment is finished, while it is judged that the predetermined time elapsed, the operation goes to Step S4, wherein the treatment similar to the above-mentioned one is conducted.

Using the moving handrail disinfecting device 10 according to the first embodiment, since it is arranged outside the inlet part 6A, maintenance work of said disinfecting device can be easily performed. Since the timing and time of conducting the disinfection operation are controlled based on the dirt state detected by the dirt detecting unit 40, the disinfection of the moving handrail 5 can be conducted at an appropriate frequency based on the dirt state and the disinfection treatment can be prevented from being conducted more than necessary, leading to reduced burden of maintenance work of the disinfection solution and the like, resulting in enhanced maintenance performance.

Since the communications unit 50 is included therein, various kinds of information obtained by said disinfecting device (information concerning the dirt state detected by the dirt detecting unit 40, the time of replacement/refilling of the applying members 11, the time of replacement/refilling of the disinfection solution tank 32, etc.) can be sent to the management center 100. In the management center 100, for example, it becomes possible to centrally manage information about a plurality of moving handrail disinfecting devices 10 installed on each escalator 1 in a facility, and it becomes possible to perform appropriate maintenance work on every moving handrail disinfecting device 10 based on these items of information, leading to improved information shareability and maintenance performance of the whole system.

Using the moving handrail disinfecting device 10, by the applying member replacing unit comprising the elevating mechanism 13, dividing mechanism 14, elevating mechanism 21, sliding mechanism 23 and associated parts, the applying member 11 (an applying member for replacement) stored in the holding frame 12 can be held by the disinfection solution supplier 24, and the (used) applying member 11 held by the disinfection solution supplier 24 can be put into the holding frame 12. That is, since the replacement of the plurality of applying members 11 can be automatically conducted without manual operation, the frequency of maintenance of replacing the applying members 11 can be reduced, resulting in improved maintenance performance.

Figure 7:
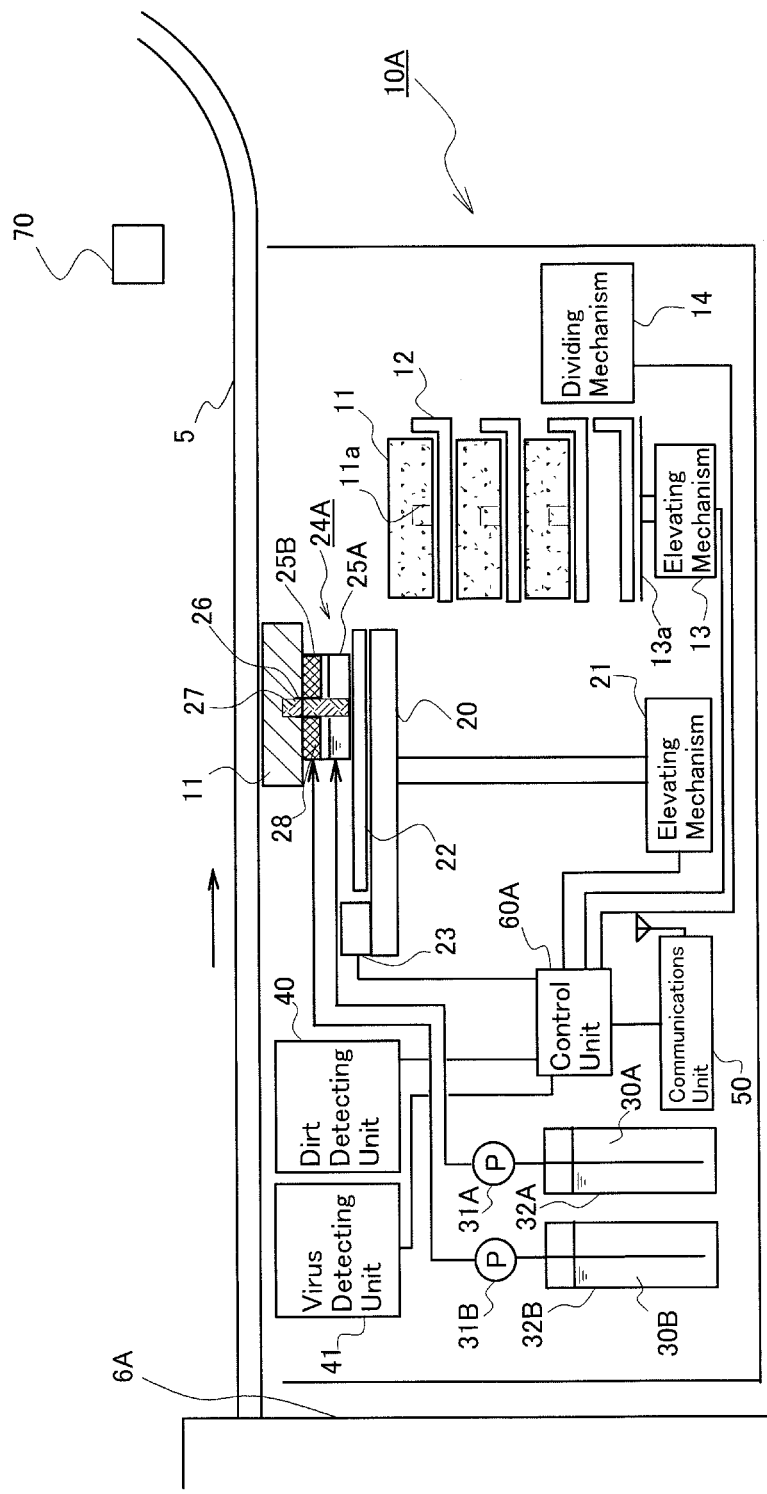
FIG. 7 is a side view schematically showing the main part of a moving handrail disinfecting device for passenger conveyor according to a second embodiment.

FIG. 7 is a side view schematically showing the main part of a moving handrail disinfecting device according to a second embodiment. Here, components having the same functions as those of the moving handrail disinfecting device 10 shown in FIG. 2 are similarly marked and are not described.

In the moving handrail disinfecting device 10 according to the first embodiment, one kind of a disinfection solution is used, while in a moving handrail disinfecting device 10A according to the second embodiment, two kinds of disinfection solutions 30A and 30B are used. In the moving handrail disinfecting device 10A according to the second embodiment, a virus detecting unit 41 is arranged besides a dirt detecting unit 40, and detection signals from a human body sensor 70 operable to detect persons who get on an escalator 1, and the like are input.

The differences in construction from the moving handrail disinfecting device 10 according to the first embodiment are described below. A disinfection solution supplier 24A comprises a first reservoir 25A in which a first disinfection solution 30A is reserved and a second reservoir 25B in which a second disinfection solution 30B is reserved, the second reservoir 25B being arranged above the first reservoir 25A.

The first reservoir 25A is connected through a first pump 31A to a first disinfection solution tank 32A, and the disinfection solution from the first disinfection solution tank 32A is automatically supplied with prescribed timing. For example, a not shown level sensor for detecting the liquid surface level is arranged within the first reservoir 25A, and when it is detected by said level sensor that the liquid surface came to a predetermined level or lower, the first disinfection solution 30A is automatically supplied.

Within the second reservoir 25B, a liquid absorbing member 28 such as a felt or a sponge is arranged in such a manner that the top of the liquid absorbing member 28 directly makes contact with an applying member 11. The disinfection solution within the second reservoir 25B is supplied (absorbed) from the liquid absorbing member 28 to (by) the applying member 11 by a capillary phenomenon. The second reservoir 25B is connected through a second pump 31B to a second disinfection solution tank 32B, and the second disinfection solution 30B from the second disinfection solution tank 32B is supplied by a fixed amount with prescribed timing. For example, when a prescribed virus was detected by the below-described virus detecting device 41, the second disinfection solution 30B is supplied by a fixed amount.

Different kinds of disinfection solutions are filled in the first disinfection solution tank 32A and the second disinfection solution tank 32B, respectively. As the first disinfection solution 30A, a disinfection solution (a cleaning solution) with a higher effect of removing dirt than the second disinfection solution 30B is used, while as the second disinfection solution 30B, a disinfection solution with better performance of sterilizing viruses and the like than the first disinfection solution 30A. For example, as the second disinfection solution 30B, an alcohol formulation having a high disinfecting/sterilizing property such as ethanol of a high concentration (about 70%-80%), a solution containing iodine of a prescribed concentration (e.g. about 0.05%-0.2%), a sodium hypochlorite solution of a prescribed concentration (e.g. about 0.01%-0.2%), a benzalkonium chloride solution of a prescribed concentration (e.g. about 0.05%-1%), or the like is used.

The virus detecting unit 41 has a function of detecting a prescribed virus (e.g. the influenza virus or the noro-virus) sticking to a moving handrail 5. Any method of detecting the virus using the virus detecting unit 41 may be adopted. For example, a detecting method such as immune-chromatography using an antigen detecting reagent of the influenza virus is adopted, wherein detection treatment (specimen sampling, specimen solution extraction, reaction treatment, decision treatment, etc.) is automatically performed. A virus detection signal detected by the virus detecting unit 41 is output to a control unit 60A.

The human body sensor 70 detects a person who gets on an escalator, comprising an infrared sensor, an image sensor and associated parts, and is installed in the vicinity of a landing of the escalator 1 or else. A signal detected by the human body sensor 70 is output to the control unit 60A. It is also possible to separately detect persons positioning on the right side and on the left side of the steps of the escalator 1 by installing a plurality of human body sensors 70.

The control unit 60A conducts control such as operation control and data sending/receiving control on each of the elevating mechanism 13, dividing mechanism 14, elevating mechanism 21, sliding mechanism 23, first pump 31A, second pump 31B, dirt detecting unit 40, virus detecting unit 41, communications unit 50 and associated parts, comprising a not shown microcomputer, an input/output interface, a memory, a timer circuit, a power circuit and associated parts.

The replacement operation of the applying members 11 conducted by the moving handrail disinfecting device 10A according to the second embodiment is similar to the replacement operation of the applying members 11 conducted by the moving handrail disinfecting device 10 according to the first embodiment, and therefore, that is not described here.

Figure 8:
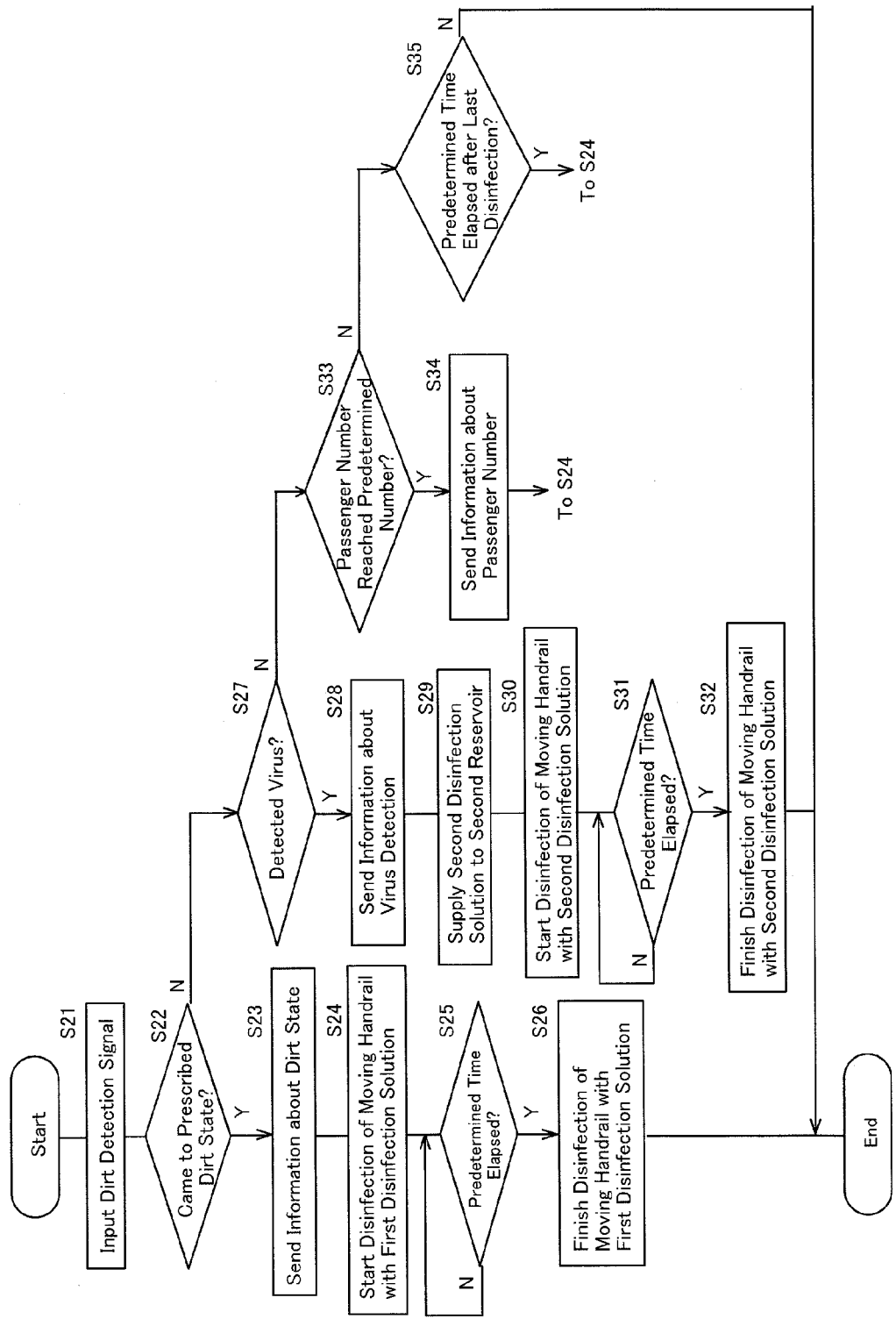
FIG. 8 is a flowchart showing a disinfection treatment operation conducted by a control unit in the moving handrail disinfecting device for passenger conveyor according to the second embodiment.

FIG. 8 is a flowchart showing a disinfection treatment operation conducted by the control unit 60A in the moving handrail disinfecting device 10A according to the second embodiment.

In Step S21, a dirt detection signal is input from the dirt detecting unit 40. In Step S22, whether the surface of the moving handrail 5 came to a prescribed dirt state or not (e.g. whether the detected number of sticking foreign materials such as dirt reached a predetermined number after the last disinfection operation or not) is judged, and when it is judged that it came to the prescribed dirt state (e.g. the detected number of sticking foreign materials reached the predetermined number), the operation goes to Step S23.

In Step S23, the communications unit 50 is controlled to send information concerning the dirt state (e.g. identification information about the device itself, elapsed time information after the last disinfection operation, and information including the detected number of sticking foreign materials) to an outside management center 100, and the operation goes to Step S24.

In Step S24, disinfection (cleaning) treatment on the moving handrail 5 using the applying member 11 moistened with the first disinfection solution 30A is started. That is, the elevating mechanism 21 is actuated to conduct control to raise a stand 20 to a situation where the applying member 11 is in contact with (is pressed against) the moving handrail 5. In Step S25, whether a predetermined time elapsed or not is judged, and when it is judged that the predetermined time elapsed, the operation goes to Step S26.

In Step S26, the elevating mechanism 21 is actuated to lower the stand 20 to a prescribed position where the applying member 11 which has been in contact with the moving handrail 5 comes off (is brought out of contact with) the moving handrail 5, and the disinfection treatment on the moving handrail 5 using the applying member 11 is completed. Here, the predetermined time is set to a previously decided uniform time, a time required for the moving handrail 5 to circuit a fixed number of times, a time decided depending on the dirt state or the like.

On the other hand, in Step S22, when it is judged that it has not come to the prescribed dirt state, the operation goes to Step S27. In Step S27, whether a virus detection signal was input from the virus detecting unit 41 or not is judged, and when it is judged that the virus detection signal was input, the operation goes to Step S28.

In Step S28, the communications unit 50 is controlled to send information concerning virus detection (e.g. identification information about the device itself and information about the detected virus) to the outside management center 100, and thereafter, the operation goes to Step S29.

In Step S29, the second pump 31B is controlled to supply the second disinfection solution 30B by a prescribed amount from the second disinfection solution tank 32B to the second reservoir 25B. In Step S30, the disinfection treatment on the moving handrail 5 using the applying member 11 moistened with the second disinfection solution 30B is started. That is, the elevating mechanism 21 is actuated to conduct control to raise the stand 20 to a situation where the applying member 11 is in contact with (is pressed against) the moving handrail 5. In Step S31, whether a predetermined time elapsed or not is judged, and when it is judged that the predetermined time elapsed, the operation goes to Step S32.

In Step S32, the elevating mechanism 21 is actuated to lower the stand 20 to a prescribed position where the applying member 11 which has been in contact with the moving handrail 5 comes off (is brought out of contact with) the moving handrail 5, and the disinfection treatment on the moving handrail 5 using the applying member 11 moistened with the second disinfection solution 30B is completed. Here, the predetermined time is set to a time required to spend almost all the second disinfection solution 30B supplied to the second reservoir 25B or the like.

On the other hand, in Step S27, when it is judged that no virus detection signal is input from the virus detecting unit 41, the operation goes to Step S33. In Step S33, whether the number of passengers after the completion of the last disinfection operation reached a predetermined number or not is judged based on a detection signal input from the human body sensor 70, and when it is judged that it reached the predetermined number, the operation goes to Step S34.

In Step S34, the communications unit 50 is controlled to send information concerning the passenger number (e.g. identification information about the device itself, elapsed time information after the last disinfection operation, and detected passenger number information) to the outside management center 100. Thereafter, the treatment in Steps S24, S25 and S26, that is, the disinfection treatment on the moving handrail 5 using the applying member 11 moistened with the first disinfection solution 30A is conducted.

On the other hand, in Step S33, when it is judged that it has not reached the predetermined number, the operation goes to Step S35. In Step S35, whether a predetermined time (e.g. several hours) elapsed after the last disinfection operation or not is judged. When it is judged that the predetermined time has not elapsed, the treatment is finished, while when it is judged that the predetermined time elapsed, the treatment in Steps S24, S25 and S26, that is, the disinfection treatment on the moving handrail 5 using the applying member 11 moistened with the first disinfection solution 30A is conducted.

Here, after the above-described disinfection treatment operation, replacement control of the applying members 11 (the same treatment as that in Steps S7-S11 shown in FIG. 6), and the disinfection solution refilling/replacement treatment on the first disinfection solution tank 32A and the second disinfection solution tank 32B (the same treatment as that in Steps S12-S15 shown in FIG. 6) are conducted.

Using the above moving handrail disinfecting device 10A according to the second embodiment, since the disinfection solution supplier 24A has the first reservoir 25A and the second reservoir 25B, it is possible to supply two kinds of disinfection solutions to the applying member 11. Since the timing of supplying the first disinfection solution 30A to the first reservoir 25A and the timing of supplying the second disinfection solution 30B to the second reservoir 25B are separately controlled based on the dirt detection state by the dirt detecting unit 40, the passenger number detected by the human body sensor 70, or the virus detection state by the virus detecting unit 41, the first disinfection solution 30A and the second disinfection solution 30B can be suitably used depending on the situations of said disinfecting device, resulting in appropriate disinfection and cleaning treatment with little waste.

When a virus is detected by the virus detecting unit 41, it is possible to disinfect the surface of the moving handrail 5 with the second disinfection solution 30B having a high disinfecting/sterilizing effect. For example, when disinfection is highly required on public health, such as when the influenza virus, the noro-virus or the like was detected, it is possible to conduct disinfection sufficiently with good timing, leading to enhanced public health.

In the management center 100, it is possible to manage the virus detection state detected by the virus detecting unit 41 of each disinfecting device 10A and to know which escalator more highly needs to be disinfected, and therefore, required maintenance work such as replacement with an appropriate disinfection solution can be performed on every disinfecting device with proper timing.

Since the timing and time of the disinfection operation are controlled based on the passenger number detected by the human body sensor 70, it is possible to disinfect the moving handrail 5 at an appropriate frequency based on the accumulated passenger number. Therefore, the disinfection treatment can be prevented from being conducted more than necessary, resulting in a reduction in maintenance cost such as disinfection solution cost.

In the management center 100, the accumulated passenger number detected by the human body sensor 70 of each disinfecting device can be managed, and therefore, required maintenance work can be performed on every disinfecting device with proper timing.

Figure 9:
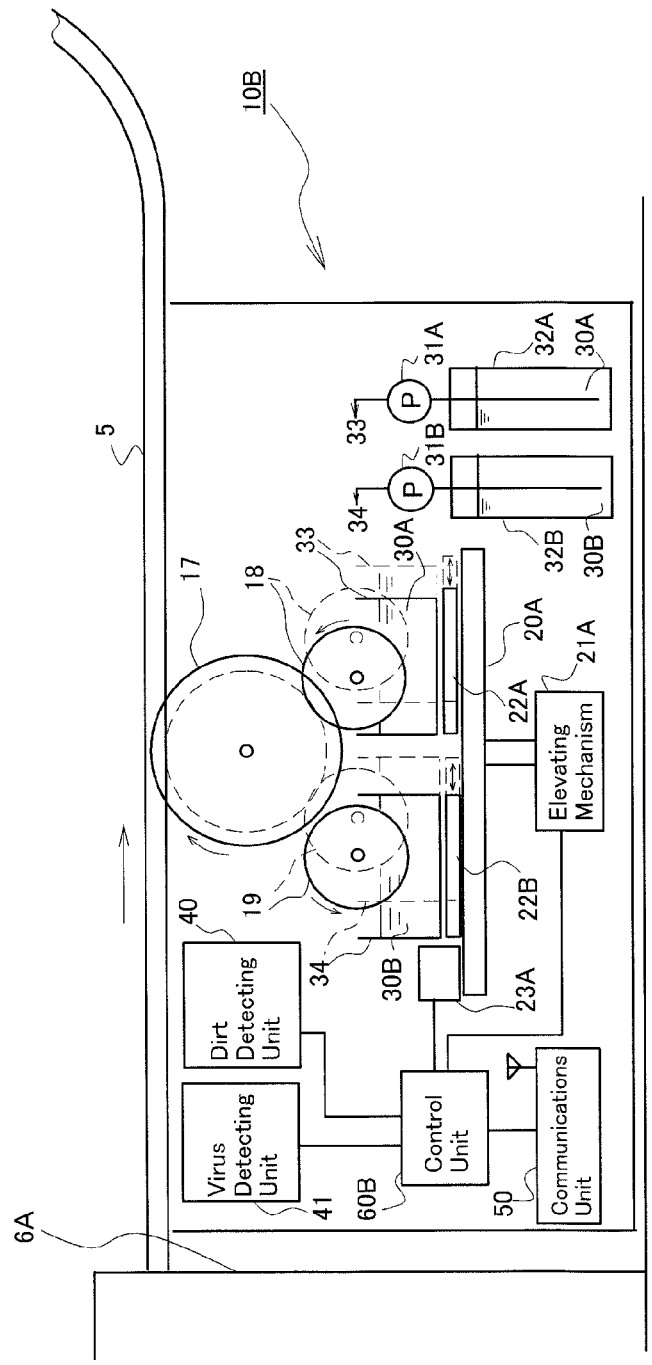
FIG. 9 is a side view schematically showing the main part of a moving handrail disinfecting device for passenger conveyor according to a third embodiment.
Figure 10:
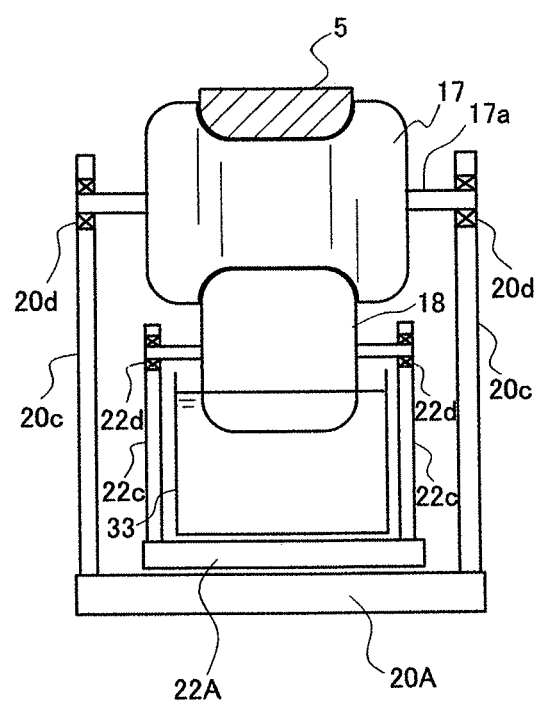
FIG. 10 is an elevation view schematically showing the main part in the vicinity of an applying roller of the moving handrail disinfecting device for passenger conveyor according to the third embodiment.

FIG. 9 is a side view schematically showing the main part of a moving handrail disinfecting device according to a third embodiment. FIG. 10 is an elevation view schematically showing the main part in the vicinity of an applying roller of the moving handrail disinfecting device according to the third embodiment. Here, the components having the same functions as those of the moving handrail disinfecting device 10A shown in FIG. 7 are similarly marked, and are not described.

A moving handrail disinfecting device 10B comprises an applying roller 17, being allowed to make contact with the surface of a moving handrail 5 having an almost C-shaped section and rotate with the movement of the moving handrail 5, a first impregnating roller 18, being allowed to make contact with the surface of the applying roller 17 and rotate, so as to supply a first disinfection solution 30A to the applying roller 17, and a second impregnating roller 19, being allowed to make contact with the surface of the applying roller 17 and rotate, so as to supply a second disinfection solution 30B to the applying roller 17.

In this embodiment, the first impregnating roller 18 and the second impregnating roller 19 are arranged in a manner that rotate in the same direction as the applying roller 17, but it is also possible to arrange them in such a manner that they rotate in the opposite direction using a driving force such as a motor.

As shown in FIG. 10, the applying roller 17 is rotatably supported with a shaft through bearing portions 20d on side walls 20c which stand on a stand 20A moving up and down. The surface of the applying roller 17 is formed almost in a U-shape in a manner that makes contact with the surface of the moving handrail 5, and it can also be allowed to make contact with the side of the moving handrail 5 having an almost C-shaped section.

On the stand 20A, a first slide plate 22A is slidably arranged, and on the first slide plate 22A, a first disinfection solution tab 33 is arranged. On both sides of the first disinfection solution tab 33, side walls 22c stand on the first slide plate 22A.

The first impregnating roller 18 is rotatably supported with a shaft through bearing portions 22d on the side walls 22c, and a part thereof is impregnated in the first disinfection solution 30A in the first disinfection solution tab 33.

On the stand 20A, a second slide plate 22B is slidably arranged, and on the second slide plate 22B, a second disinfection solution tab 34 is arranged. On both sides of the second disinfection solution tab 34, side walls (not shown) stand on the second slide plate 22B.

The second impregnating roller 19 is rotatably supported with a shaft through bearing portions (not shown) on the side walls, and a part thereof is impregnated in the second disinfection solution 30B in the second disinfection solution tab 34.

The moving handrail disinfecting device 10B comprises an elevating mechanism 21A operable to raise and lower the stand 20A, and a sliding mechanism 23A operable to allow the first slide plate 22A and the second slide plate 22B to separately slide crossing at right angles to a rotating shaft 17a of the applying roller 17. As the construction of the elevating mechanism 21A or the sliding mechanism 23A, an electromagnetic actuator having a stretching mechanism, a motor-driven cam mechanism, or various kinds of driving mechanisms wherein a gear mechanism such as a worm gear or a rack and pinion and a motor are combined may be adopted.

A contact roller switching mechanism (a contact roller switching unit) which switches the roller to be allowed to make contact with the applying roller 17 to the first impregnating roller 18 or the second impregnating roller 19, comprises the first slide plate 22A, second slide plate 22B and sliding mechanism 23A. The disinfecting unit comprises the applying roller 17, first impregnating roller 18, and second impregnating roller 19, and said contact roller switching mechanism.

The bearing portions 20d of the applying roller 17, the bearing portions 22d of the first impregnating roller 18 and the bearing portions (not shown) of the second impregnating roller 19 are constructed in such a manner that rotation sliding resistance is given to the rotation movement of the rotation shaft of each roller. Because of this rotation sliding resistance, the rotation rate of the applying roller 17 is regulated to be slower than the moving rate of the moving handrail 5, and due to the effect of the rotation sliding resistance between the applying roller 17 and the moving handrail 5, the efficiency of applying the disinfection solution, that of removing dirt and the like are enhanced.

To the first disinfection solution tab 33, a first disinfection solution tank 32A is connected through a first pump 31A, and the first disinfection solution 30A is supplied to the first disinfection solution tab 33 from the first disinfection solution tank 32A with prescribed timing. For example, with the timing when it is detected that the liquid surface came to a predetermined level or lower by a not shown level sensor operable to detect the liquid surface level arranged within the first disinfection solution tab 33, the first disinfection solution 30A is supplied to the first disinfection solution tab 33.

To the second disinfection solution tab 34, a second disinfection solution tank 32B is connected through a second pump 31B, and the second disinfection solution 30B is supplied to the second disinfection solution tab 34 from the second disinfection solution tank 32B with prescribed timing. For example, with the timing when it is detected that the liquid surface came to a predetermined level or lower by a not shown level sensor operable to detect the liquid surface level arranged within the second disinfection solution tab 34, the second disinfection solution 30B is supplied to the second disinfection solution tab 34.

Different kinds of disinfection solutions are filled in the first disinfection solution tank 32A and the second disinfection solution tank 32B, respectively. As the first disinfection 30A, a disinfection solution (a cleaning solution) with a higher effect of removing dirt than the second disinfection solution 30B is used, while as the second disinfection solution 30B, a disinfection solution with better sterilization performance of viruses and the like than the first disinfection solution 30A is used.

As the second disinfection solution 30B, for example, an alcohol formulation having a high disinfecting/sterilizing property such as ethanol of a high concentration (about 70%-80%), a solution containing iodine of a prescribed concentration (e.g. about 0.05%-0.2%), a sodium hypochlorite solution of a prescribed concentration (e.g. about 0.01%-0.2%), a benzalkonium chloride solution of a prescribed concentration (e.g. about 0.05%-0.1%) or the like is used.

A handrail sensor 71 is a sensor operable to detect a passenger's holding onto the moving handrail 5. The handrail sensors 71 each are arranged above the moving handrails 5 on both sides or on the side walls of the building in the vicinity of a landing of the escalator 1 or several steps forward from the landing. The handrail sensor 71 detects the existence of an object on the moving handrail 5 within a given detecting area, and using the handrail sensor 71, it is possible to detect passengers' holding onto the moving handrail 5 separately on both of the moving handrails 5. The handrail sensor 71 comprises an image sensor and an image processor, and a signal detected by the handrail sensor 71 is output to a control unit 60B.

The control unit 60B conducts control of operations and control of sending/receiving of data on each of the elevating mechanism 21A, sliding mechanism 23A, first pump 31A, second pump 31B, dirt detecting unit 40, virus detecting unit 41, communications unit 50 and associated parts, comprising a not shown microcomputer, an input/output interface, a memory, a timer circuit, a power circuit and associated parts.

The control unit 60B has a control function of switching the roller to be allowed to make contact with the applying roller 17 from the first impregnating roller 18 to the second impregnating roller 19 when a virus was detected by the virus detecting unit 41 (a first switching condition), and a control function of switching the roller to be allowed to make contact with the applying roller 17 from the second impregnating roller 19 to the first impregnating roller 18 when the dirt state detected by the dirt detecting unit 40 came to a prescribed dirt state (a second switching condition).

Figure 11:
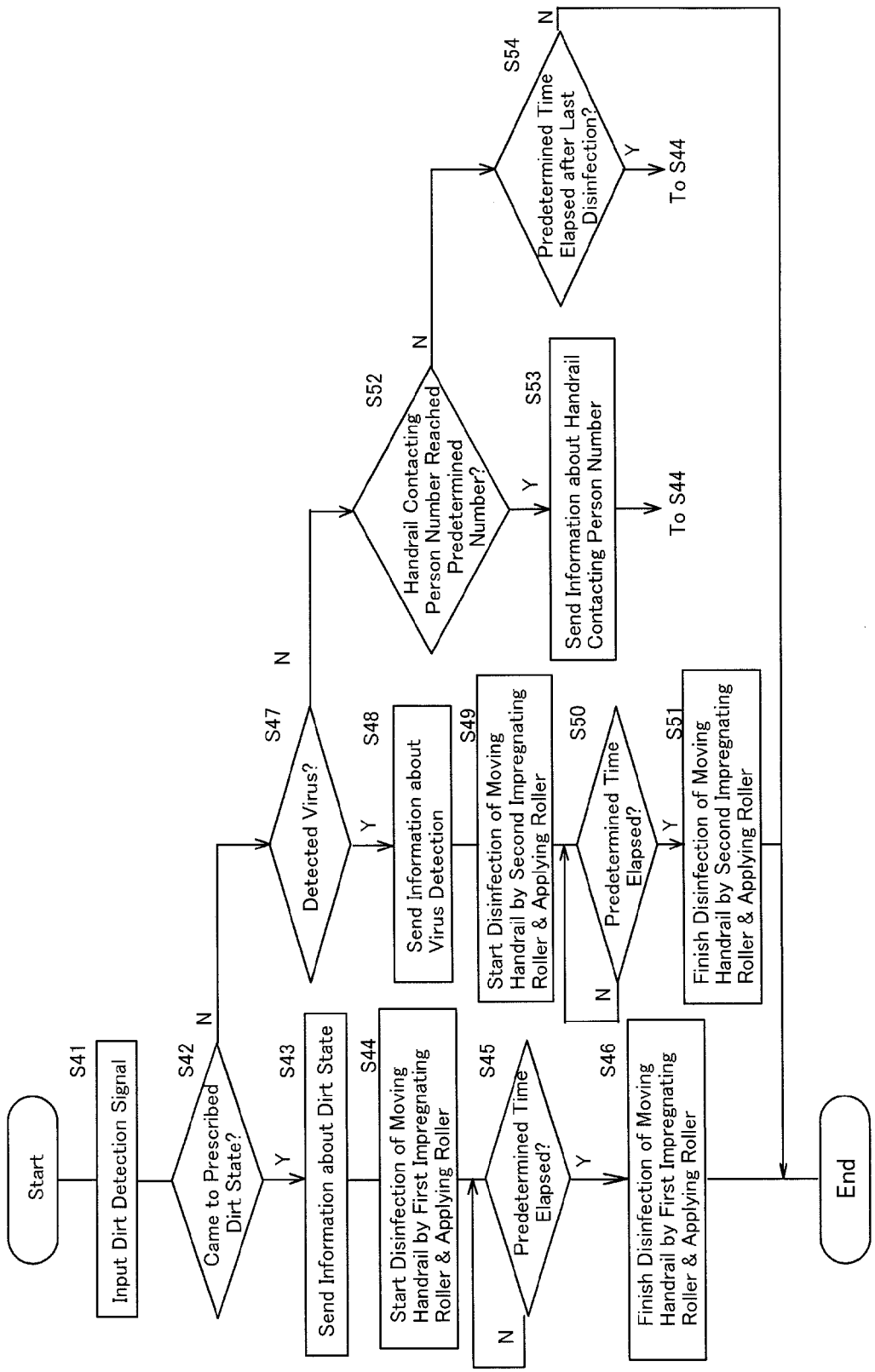
FIG. 11 is a flowchart showing a disinfection treatment operation conducted by a control unit in the moving handrail disinfecting device for passenger conveyor according to the third embodiment.

FIG. 11 is a flowchart showing the disinfection treatment operation conducted by the control unit 60B in the moving handrail disinfecting device 10B according to the third embodiment.

In Step S41, a dirt detection signal is input from the dirt detecting unit 41, and in Step S42, whether the surface of the moving handrail 5 came to the prescribed dirt state or not (e.g. whether the detected number of sticking foreign materials such as dirt reached a predetermined number after the last disinfection operation or not) is judged. When it is judged that it came to the prescribed dirt state (e.g. the detected number of sticking foreign materials reached the predetermined number), the operation goes to Step S43.

In Step S43, the communications unit 50 is controlled to send information concerning the dirt state (e.g. identification information about the device itself, elapsed time information after the last disinfection operation, and information including the detected number of sticking foreign materials) to an outside management center 100, and the operation goes to Step S44.

In Step S44, the disinfection (cleaning) treatment on the moving handrail 5 using the first impregnating roller 18 moistened with the first disinfection solution 30A and the applying roller 17 is started. That is, the sliding mechanism 23A is actuated to slide the first slide plate 22A in such a manner that the first impregnating roller 18 comes in contact with the applying roller 17, while to slide the second slide plate 22B in such a manner that the second impregnating roller 19 does not come in contact with the applying roller 17.

Thereafter, the elevating mechanism 21A is actuated to raise the stand 20A to a situation where the applying roller 17 is in contact with (is pressed against) the moving handrail 5, and the disinfection (cleaning) treatment is started.

In Step S45, whether a predetermined time elapsed or not is judged, and when it is judged that the predetermined time elapsed, the operation goes to Step S46. In Step S46, the elevating mechanism 21A is actuated to lower the stand 20A to a prescribed position where the applying roller 17 which has been in contact with the moving handrail 5 comes off (is brought out of contact with) the moving handrail 5, and this is the completion of the disinfection treatment on the moving handrail 5 using the applying roller 17. Here, the above predetermined time is set to a previously decided uniform time, a time required for the moving handrail 5 to circuit a fixed number of times, a time decided depending on the dirt state, or the like.

On the other hand, in Step S42, when it is judged that it has not come to the prescribed dirt state, the operation goes to Step S47. In Step S47, whether a virus detection signal was input from the virus detecting unit 41 or not is judged, and when it is judged that the virus detection signal was input, the operation goes to Step S48.

In Step S48, the communications unit 50 is controlled to send information concerning the virus detection (e.g. identification information about the device itself and information about the detected virus) to the management center 100, and thereafter, the operation goes to Step S49.

In Step S49, the disinfection treatment on the moving handrail 5 using the second impregnating roller 19 moistened with the second disinfection solution 30B and the applying roller 17 is started. That is, the sliding mechanism 23A is actuated to slide the second slide plate 22B in such a manner that the second impregnating roller 19 comes in contact with the applying roller 17, while to slide the first slide plate 22A in such a manner that the first impregnating roller 18 does not come in contact with the applying roller 17. Thereafter, the elevating mechanism 21A is actuated to raise the stand 20A to a situation where the applying roller 17 is in contact with (is pressed against) the moving handrail 5, and the disinfection treatment is started.

In Step S50, whether a predetermined time elapsed or not is judged, and when it is judged that the predetermined time elapsed, the operation goes to Step S51. In Step S51, the elevating mechanism 21A is actuated to lower the stand 20A to a prescribed position where the applying roller 17 which has been in contact with the moving handrail 5 comes off (is brought out of contact with) the moving handrail 5, and the disinfection treatment on the moving handrail 5 using the applying roller 17 moistened with the second disinfection solution 30B is completed.

On the other hand, in Step S47, when it is judged that no virus detection signal has been input from the virus detecting unit 41, the operation goes to Step S52. In Step S52, based on a detection signal input from the handrail sensor 71, whether the number of persons who made contact with the moving handrail 5 after the completion of the last disinfection operation reached a predetermined number or not is judged, and when it is judged that it reached the predetermined number, the operation goes to Step S53.

In Step S53, the communications unit 50 is controlled to send information concerning the number of handrail contacting persons (e.g. identification information about the device itself, elapsed time information after the last disinfection operation and the detected handrail contacting person number information) to the management center 100, and thereafter, the treatment in Steps S44, S45 and S46, that is, the disinfection treatment on the moving handrail 5 using the applying roller 17 moistened with the first disinfection solution 30A is conducted.

On the other hand, in Step S52, when it is judged that it has not reached the predetermined number, the operation goes to Step S54. In Step S54, whether a predetermined time (e.g. several hours) elapsed after the last disinfection operation or not is judged, and when it is judged that the predetermined time has not elapsed, the operation is finished, while when it is judged that the predetermined time elapsed, the treatment in Steps S44, S45 and S46, that is, the disinfection treatment on the moving handrail 5 using the applying roller 17 moistened with the first disinfection solution 30A is conducted.

Here, after the above-described disinfection treatment operation, the refilling/replacement treatment operation of the disinfection solutions to the first disinfection solution tank 32A and the second disinfection solution tank 32B is conducted.

Using the moving handrail disinfecting device 10B according to the third embodiment, when a virus was detected by the virus detecting unit 41, the roller to be allowed to make contact with the applying roller 17 can be switched from the first impregnating roller 18 to the second impregnating roller 19, resulting in appropriate disinfection of the surface of the moving handrail 5 with the second disinfection solution 30B having a high disinfection effect. It becomes possible to suitably use two kinds of disinfection solutions depending on the situations of said disinfecting device and the like, leading to appropriate disinfection treatment with little waste depending on the situations.

Since the bearing portions 20*d* of the applying roller 17, the bearing portions 22*d* of the first impregnating roller 18 and the bearing portions (not shown) of the second impregnating roller 19 are constructed in such a manner that rotation sliding resistance is given to the rotation movement of the rotation shaft of each roller, it is possible to regulate the rotation rate of the applying roller 17 to be slower than the moving rate of the moving handrail 5. By causing the rotation sliding resistance (a slippage state) between the applying roller 17 and the moving handrail 5, the efficiency of applying disinfection solutions and that of removing dirt can be enhanced.

Since the timing and time of the disinfection operation with the first disinfection solution 30A by allowing the first impregnating roller 18 to make contact with the applying roller 17 is controlled based on the number of handrail contacting persons detected by the handrail sensor 71, the disinfection of each of the moving handrails 5 arranged on both sides can be separately conducted at an appropriate frequency based on the accumulated number of persons which made contact with the moving handrail 5 and the like. As a result, it becomes possible to prevent the disinfection (cleaning) treatment from being conducted more than necessary, leading to a reduction in maintenance cost such as disinfection solution cost.

By sending information from the communications unit 50 to the management center 100, the handrail contact detection state detected by the handrail sensor 71 of each disinfecting device can be managed, and it becomes possible to perform required maintenance work with proper timing on every disinfecting device.

Here, in the above-described moving handrail disinfecting device 10B, the dirt detecting unit 40 and the virus detecting unit 41 are arranged, but in another embodiment, it is possible to arrange a virus detecting unit 41 while to arrange no dirt detecting unit 40. By such construction, only when a prescribed virus was detected by the virus detecting unit 41, the roller to be allowed to make contact with an applying roller 17 may be switched from a first impregnating roller 18 to a second impregnating roller 19 to conduct a disinfection operation with a second disinfection solution 30B for a predetermined time. Under normal conditions besides that, the first impregnating roller 18 may be allowed to make contact with the applying roller 17 to continuously go on with the disinfection (cleaning) treatment on a moving handrail 5 using the applying roller 17 moistened with a first disinfection solution 30A.

In still another embodiment, with no dirt detecting unit 40 and no virus detecting unit 41 arranged, based on detection signals from a handrail sensor 71, the switching of a roller to be allowed to make contact with an applying roller 17 may be conducted. For example, when the number of handrail contacting persons reached a predetermined number, a first impregnating roller 18 may be allowed to make contact with the applying roller 17 to conduct disinfection (cleaning) with a first disinfection solution 30A, while when a predetermined time elapsed, a second impregnating roller 19 may be allowed to make contact with the applying roller 17 to periodically conduct disinfection with a second disinfection solution 30B. In place of the handrail sensor 71, a human body sensor 70 may be used.

In another embodiment of the moving handrail disinfecting devices 10, 10A and 10B according to the first to third embodiments, respectively, a drying unit which promotes drying of an applied disinfection solution by blowing a hot wind onto the surface of a moving handrail 5 or the like may be arranged. Or a wiping member for wiping away an extra amount of a disinfection solution attached to the surface of the moving handrail 5 may be arranged.

The moving handrail disinfecting devices 10, 10A and 10B may be applied to other passenger conveyors such as so-called moving pavements, which allow passengers to go in a horizontal direction or in a slightly inclined direction.

What is claimed is:

1. A moving handrail disinfecting device for passenger conveyor for disinfecting a moving handrail circuiting in synchronism with steps of a passenger conveyor, comprising:
   a disinfecting unit operable to disinfect the surface of the moving handrail, being installed outside at least one of handrail inlets on each side of drawing and delivery of the moving handrail;
   a control unit operable to control disinfection operations by the disinfecting unit based on prescribed operating conditions; and
   a communications unit operable to send information obtained by said disinfecting device to an outside management center,
   the disinfecting unit comprising:
   a storage section which can separately store a plurality of applying members;
   a disinfection solution supply section operable to hold an applying member taken from said storage section, as well as supply a disinfection solution to said held applying member; and
   an applying member replacing section having a function of allowing the disinfection solution supply section to hold the applying member stored in the storage section, as well as a function of putting the applying member held by the disinfection solution supply section into the storage section,
   wherein the applying member held by the disinfection solution supply section is allowed to make contact with the surface of the moving handrail to apply the disinfection solution.

2. The moving handrail disinfecting device for passenger conveyor according to claim 1, wherein the disinfection solution supply section constituting the disinfecting unit has a first reservoir which can reserve a first disinfection solution and a second reservoir which can reserve a second disinfection solution; and
   the control unit separately controls the timing of supplying the first disinfection solution to the first reservoir and the timing of supplying the second disinfection solution to the second reservoir.

3. The moving handrail disinfecting device for passenger conveyor according to claim 1, further comprising:
   a dirt detecting unit operable to detect dirt on the surface of the moving handrail,
   wherein the control unit controls the timing and time of a disinfection operation by the disinfecting unit based on the state of dirt detected by the dirt detecting unit; and
   the control unit controls the communications unit to send information about the state of dirt detected by the dirt detecting unit to the management center.

4. The moving handrail disinfecting device for passenger conveyor according to claim 1, further comprising:
   a passenger number detecting unit operable to detect the number of persons boarding the passenger conveyor,
   wherein the control unit controls the timing and time of a disinfection operation by the disinfecting unit based on the accumulated number of passengers detected by the passenger number detecting unit; and
   the control unit controls the communications unit to send information about the accumulated number of passengers detected by the passenger number detecting unit to the management center.

5. The moving handrail disinfecting device for passenger conveyor according to claim 1, further comprising:
   a handrail contact detecting unit operable to detect a contact of a part of a body with the moving handrail,
   wherein the control unit controls the timing and time of a disinfection operation by the disinfecting unit based on the detection state of handrail contact detected by the handrail contact detecting unit; and
   the control unit controls the communications unit to send information about the detection state of handrail contact detected by the handrail contact detecting unit to the management center.

6. The moving handrail disinfecting device for passenger conveyor according to claim 1, further comprising:
   a virus detecting unit operable to detect a prescribed virus sticking to the surface of the moving handrail, wherein the control unit controls the timing and time of a disinfection operation by the disinfecting unit based on the detection state of the virus detected by the virus detecting unit; and the control unit controls the communications unit to send information about the detection state of the prescribed virus detected by the virus detecting unit to the management center.

7. A moving handrail disinfecting device for passenger conveyor for disinfecting a moving handrail circuiting in synchronism with steps of a passenger conveyor, comprising:

a disinfecting unit operable to disinfect the surface of the moving handrail, being installed outside at least one of handrail inlets on each side of drawing and delivery of the moving handrail; and a control unit operable to control disinfection operations by the disinfecting unit based on prescribed operating conditions, the disinfecting unit comprising:

a storage section which can separately store a plurality of applying members;

a disinfection solution supply section operable to hold an applying member taken from said storage section, as well as supply a disinfection solution to said held applying member; and an applying member replacing section having a function of allowing the disinfection solution supply section to hold the applying member stored in the storage section, as well as a function of putting the applying member held by the disinfection solution supply section into the storage section, wherein the applying member held by the disinfection solution supply section is allowed to make contact with the surface of the moving handrail to apply the disinfection solution.

8. The moving handrail disinfecting device for passenger conveyor according to claim 7, wherein the disinfection solution supply section constituting the disinfecting unit has a first reservoir which can reserve a first disinfection solution and a second reservoir which can reserve a second disinfection solution; and the control unit separately controls the timing of supplying the first disinfection solution to the first reservoir and the timing of supplying the second disinfection solution to the second reservoir.

9. The moving handrail disinfecting device for passenger conveyor according to claim 2, further comprising:

a dirt detecting unit operable to detect dirt on the surface of the moving handrail, wherein the control unit controls the timing and time of a disinfection operation by the disinfecting unit based on the state of dirt detected by the dirt detecting unit; and the control unit controls the communications unit to send information about the state of dirt detected by the dirt detecting unit to the management center.

10. The moving handrail disinfecting device for passenger conveyor according to claim 2, further comprising:

a passenger number detecting unit operable to detect the number of persons boarding the passenger conveyor, wherein the control unit controls the timing and time of a disinfection operation by the disinfecting unit based on the accumulated number of passengers detected by the passenger number detecting unit; and the control unit controls the communications unit to send information about the accumulated number of passengers detected by the passenger number detecting unit to the management center.

11. The moving handrail disinfecting device for passenger conveyor according to claim 2, further comprising:

a handrail contact detecting unit operable to detect a contact of a part of a body with the moving handrail, wherein the control unit controls the timing and time of a disinfection operation by the disinfecting unit based on the detection state of handrail contact detected by the handrail contact detecting unit; and the control unit controls the communications unit to send information about the detection state of handrail contact detected by the handrail contact detecting unit to the management center.

12. The moving handrail disinfecting device for passenger conveyor according to claim 2, further comprising:

a virus detecting unit operable to detect a prescribed virus sticking to the surface of the moving handrail, wherein the control unit controls the timing and time of a disinfection operation by the disinfecting unit based on the detection state of the virus detected by the virus detecting unit; and the control unit controls the communications unit to send information about the detection state of the prescribed virus detected by the virus detecting unit to the management center.

* * * * *